United States Patent [19]

Roy et al.

[11] 4,143,316

[45] Mar. 6, 1979

[54] HYDROGEN CONSENTRATION METER UTILIZING A DIFFUSION TUBE COMPOSED OF 2 ¼ CR-1 MO STEEL AND A SLEEVE OF NICKEL

[75] Inventors: Prodyot Roy, Saratoga; David W. Sandusky; Robert T. Hartle, both of San Jose, all of Calif.

[73] Assignee: The United States of America as represented by the United States Department of Energy, Washington, D.C.

[21] Appl. No.: 831,191

[22] Filed: Sep. 7, 1977

[51] Int. Cl.² ............... G01N 27/00; G01N 27/62
[52] U.S. Cl. ................................ 324/33; 73/19; 73/23; 55/158; 204/195 P
[58] Field of Search ............... 324/33; 73/19, 23; 55/158; 204/195 P

[56] References Cited

U.S. PATENT DOCUMENTS

| | | | |
|---|---|---|---|
| 3,350,846 | 11/1967 | Makrides et al. | 55/158 |
| 3,731,523 | 5/1973 | Vissers et al. | 73/19 |
| 3,886,444 | 5/1975 | Roy et al. | 324/33 |

Primary Examiner—Robert J. Corcoran
Attorney, Agent, or Firm—Dean E. Carlson; R. S. Gaither; L. E. Carnahan

[57] ABSTRACT

A diffusion tube hydrogen meter for improving the sensitivity and response time for the measurement of hydrogen in liquid sodium. The improved hydrogen meter has a composite membrane composed of pure nickel sleeve fitted, for example, over a 2 ¼ Cr-1 Mo steel or niobium diffusion tube. Since the hydrogen permeation rate through 2 ¼ Cr-1 Mo steels is a factor of four higher than pure nickel, and the permeation rate of hydrogen through niobium is two orders of magnitude greater than the 2 ¼ Cr-1 Mo steel, this results in a decrease in response time and an increase in the sensitivity.

5 Claims, 3 Drawing Figures

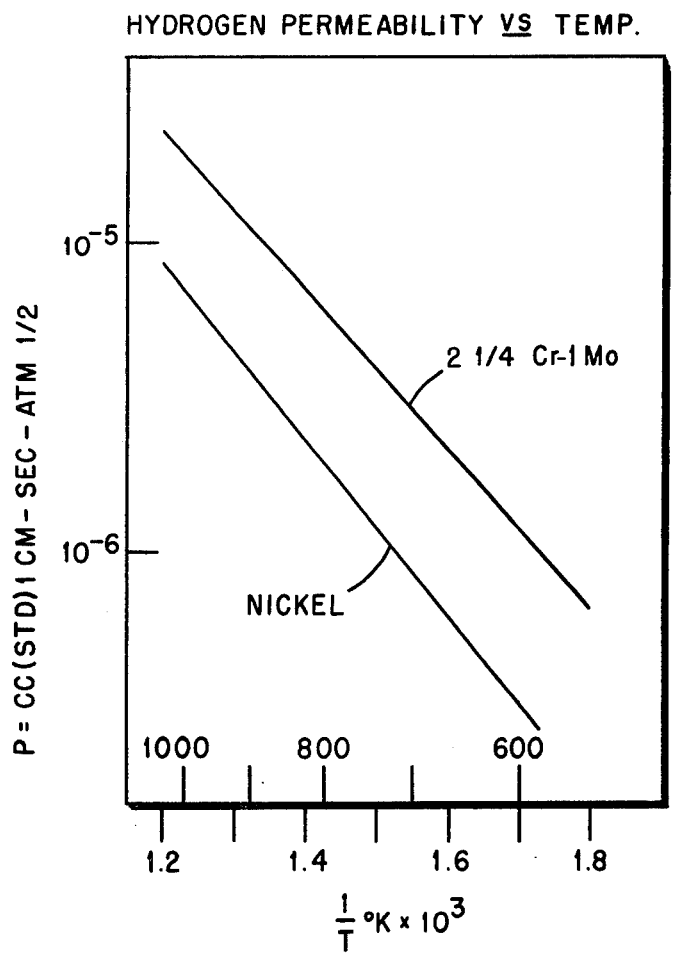
*Fig 1*
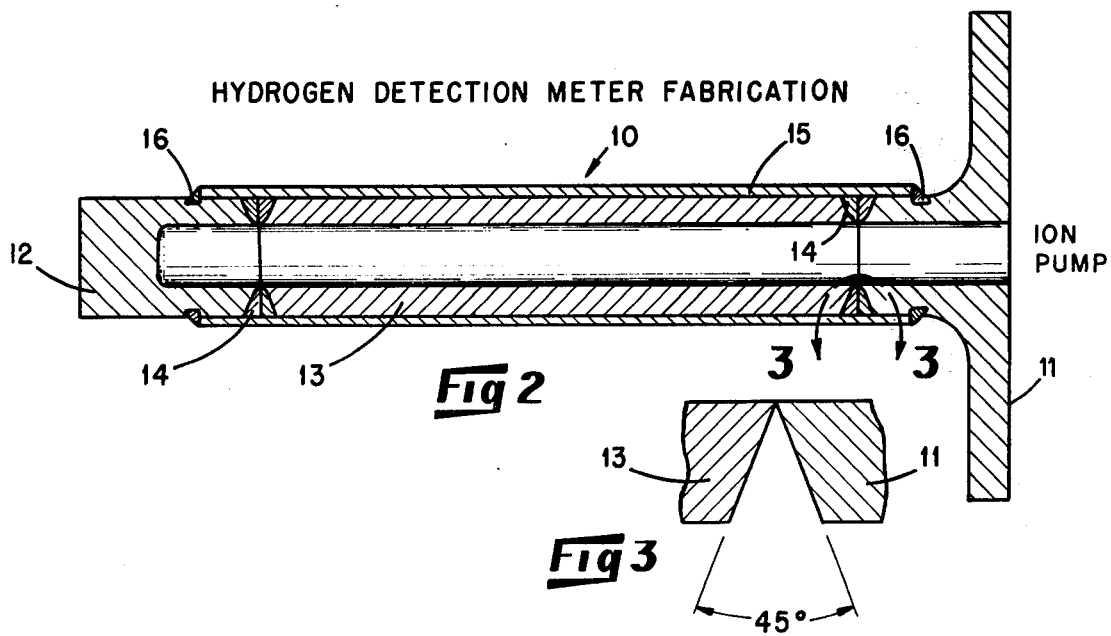
*Fig 2*
*Fig 3*

HYDROGEN CONSENTRATION METER UTILIZING A DIFFUSION TUBE COMPOSED OF 2¼ CR-1 MO STEEL AND A SLEEVE OF NICKEL

BACKGROUND OF THE INVENTION

The invention described herein was made in the course of, or under, a contract with the United States Energy Research and Development Administration.

This invention relates to the measurement of hydrogen in liquid sodium, particularly to a diffusion tube hydrogen meter, and more particularly to an improved composite diffusion tube assembly for hydrogen meters.

The type and levels of impurities in liquid sodium coolant, such as the hydrogen concentration level, has caused concern in the development of sodium-cooled nuclear reactors. As known, hydrogen can enter the sodium coolant in a number of ways. Various detectors, known as leak detectors have been developed for determining impurities, such as hydrogen, in liquid metal sodium. These prior known hydrogen detectors are exemplified by U.S. Pat. Nos. 3,683,272 issued Aug. 8, 1972; 3,731,523 issued May 8, 1973; and 3,886,444 issued May 27, 1975.

Previously, the hydrogen concentrations in liquid sodium are measured by a diffusion tube hydrogen meter. This meter essentially consists of a thin nickel diffusion membrane connected to the vacuum system operated with an ion pump. The nickel diffusion tube is inserted into the liquid sodium; the hydrogen dissolved in sodium diffuses through the membrane into the vacuum. The flux of hydrogen diffusing through the membrane is measured by current of the ion pump. Since the flux of the hydrogen diffusion through the membrane is proportional to the hydrogen concentration in liquid sodium, the ion current output of the pump can be readily translated into the concentration of hydrogen in liquid sodium.

The sensitivity of these hydrogen meters (microamps/ppb H in Na) is proportional to A/L, where A=λ surface area of the membrane, and L=thickness of the membrane used in the meter. The response time (time required by the ion pump to detect a step change in the hydrogen concentration in sodium), is directly proportional to $L^2$. The previously utilized hydrogen ($H_2$) meters consist of a pure nickel tube (for example, 0.5 inch outside diameter and 14 mils wall) with an approximate surface area of 7in$^2$. With this configuration, the response time of the existing meters is about 24 seconds, and the sensitivity is approximately 0.13 micro amps/ppb H in Na (with a standard 8l/sec ion pump).

SUMMARY OF THE INVENTION

The present invention is directed to a hydrogen meter utilizing an improved composite diffusion tube assembly whereby the response time is decreased and the sensitivity is increased. The hydrogen meter of this invention uitilizes a pure nickel sleeve shrink fitted, or otherwise provided, over a 2¼ Cr-1 Mo steel or niobium diffusion tube. This produces a reduction in response time in comparison to the times of the previously known meters by a factor of four (from about 24 to about 6 sec) using 2¼ Cr-Mo, and the sensitivity is twice that of the prior art meters. Both of these improvements are extremely valuable from the standpoint of detection of steam or water leaks in sodium heated steam generators. Utilizing a niobium diffusion tube, the response time is further reduced and the sensitivity is greater.

Therefore, it is an object of this invention to provide an improved diffusion tube hydrogen meter.

A further object of the invention is to provide a hydrogen meter that reduces response time while increasing sensitivity.

Another object of the invention is to provide a hydrogen meter which uses a pure nickel sleeve over a chromium-molybdenum diffusion tube.

Another object of the invention is to provide a hydrogen meter which uses a niobium diffusion tube.

Other objects of the invention will become readily apparent from the following description and accompanying drawings.

BRIEF DESCRIPTION OF THE DRAWINGS

FIG. 1 graphically illustrates hydrogen permeability vs. temperature;

FIG. 2 is a partial view partially in cross-section, of a low alloy steel diffusion tube assembly for a hydrogen meter made in accordance with the invention; and FIG. 3 is an enlarged view of a section of the FIG. 2 diffusion tube assembly with welding omitted for clarity.

DESCRIPTION OF THE INVENTION

The present invention is a hydrogen meter utilizing an improved composite diffusion tube assembly which improves the response time and the sensitivity of previously utilized diffusion tube hydrogen meters, which is vitally important for early detection of steam or water leaks in sodium heated steam generators.

Improving the response time and the sensitivity of the known hydrogen meters could be achieved by reducing the diffusion time of hydrogen through the membrane (diffusion tube). Obviously, reduction of the nickel membrane thickness is one of the solutions. However, stress analysis based on mechanical property data of pure nickel (Ni) indicates that a minimum thickness of 14 mils is required to prevent the collapse of the membrane at operating pressure (340 psig) and temperature (~900° F.). The other alternative is to use a membrane material which has a higher hydrogen diffusion rate. In principle, several materials, e.g., palladium (Pd), niobium (Nb), and 2¼ chromium (Cr)-1 molybdenum (Mo) can be used. While testing of a 2¼ Cr-1 Mo diffusion membrane showed encouraging results, the performance degraded with time due to the deposition of a thin layer of chromium on the membrane, which effectively reduced the permeation rate of hydrogen through the membrane. The permeation rate for hydrogen through 2¼ Cr-1 Mo steels is about four times higher than pure nickel, as shown in FIG. 1. Furthermore, this material is considerably stronger than pure nickel. Consequently, it has been determined that 10 mils thick 2¼ Cr-1 Mo membrane is capable of sustaining the operating pressures and temperature involved in sodium heated steam generator applications, for example.

The present invention broadly consists of a diffusion tube assembly for a hydrogen meter which includes a composite membrane consisting of a pure nickel sleeve shrink fitted or otherwise provided over a niobium or 2¼ Cr-1 Mo steel diffusion tube as illustrated in FIG. 2. The diffusion tube assembly is connected to an ion pump having a power supply and current readout means, not shown, but similar to that illustrated in above-referenced U.S. Pat. No. 3,886,444.

While the following description is directed to the low alloy (2¼ Cr-1 Mo) steel, it is not intended to limit the invention since tests have shown that niobium can also be utilized.

Referring now to the drawings, the diffusion tube assembly, indicated generally at 10 consists of flange member 11 and an end cap member 12 interconnected by a diffusion tube 13 via weld joints 14, and a sleeve 15 extending around tube 13 and secured by weld joints 16 to members 11 and 12. Members 11 and 12 are constructed, for example, of 304 stainless steel (SST), tube 13 being constructed of 10 mil thick 2¼ Cr-1 Mo steel, with sleeve 15 being constructed of 4 mil thick pure nickel. FIG. 2a illustrates a 45° groove between tube 13 and end members 11 and 12 wherein welds 16 are made as described hereinafter. It is understood that the invention is not limited to the specific thickness of the composite membrane (tube 13 and sleeve 15) exemplified above, as other thicknesses may be utilized. The diffusion tube assembly 10 is connected via flange member 11 to an ion pump indicated by legend, as known in the art.

Since the hydrogen permeation rate through 2¼ Cr-1 Mo steels is a factor of four higher than pure nickel, the 10 mils of 2¼ Cr-1 Mo steel is equivalent to having a 2.5 mils pure nickel membrane. Consequently, the total membrane thickness of the composite membrane (tube 13 and sleeve 15) is equivalent to 6.5 mils of pure nickel. The reduction of the membrane thickness from 14 mils minimum used previously, to 6.5 mils corresponds to a decrease in the response time by a factor of four (from about 24 seconds to about 6 seconds). If the surface area of the membrane is kept constant, the sensitivity of the instrument (hydrogen meter) is inversely proportional to the thickness of the membrane. Hence, for the same membrane surface area (7in$^2$), utilized previously, the sensitivity of the above-described improved hydrogen meter of this invention will be a factor of two greater than the previous meters (0.13 micro amps/ppb H to 0.26 micro amps/ppb H).

The method of fabrication of the above-described embodiment of the invention is as follows:

1. Machine weld preps on 2¼ Cr-1 Mo and SST 304 as shown on FIGS. 2 and 2a. Clean with trisodium phosphate solution.
2. Weld (GTAW) 2¼ Cr-1 Mo tube 13 ends to SST 304 flange 11 and end cap 12 using Inco 82 filler wire as per FIG. 2. Preheat 400° F.
3. Post weld heat treat joints 14 and 1340° F. ± 35° F. for one hour, air cool.
4. Machine end cap 12, tube 13 and weld joints 14 and tubular section of flange member 11 outside diameter (O.D.) to +0.0000″ 1−0.0005″; smooth to a 24 (RMS) finish or between. Clean with acetone.
5. Shrink fit nickel 201 sleeve 15 onto assembly (end cap 12, tube 13 and flange member 11) into position as shown in FIG. 2.
6. Heliarc seal weld nickel sleeve 15 to SST 304 end cap 12 and flange member 11 as per FIG. 2.

It has thus been shown that the use of the above-described embodiment of the composite membrane of the present invention will reduce the response time of the previous hydrogen (H$_2$) meters by a factor of four (24 to 6 sec.), with the sensitivity of the improved H$_2$ meter being twice that of the previous meters. Both of these improvements are extremely valuable from the standpoint of detection of steam or water leaks in sodium heated steam generators.

Recent tests have shown, that niobium can be substituted for the above-described low alloy steel. The permeability of hydrogen through niobium exceeds the low alloy steel or nickel by approximately two orders of magnitude at 500° C. such that the thin nickel layer limits hydrogen permeation rather than the niobium support tube. Therefore, with respect to hydrogen permeation the effective membrane thickness is reduced to the thickness of the nickel plating (<50μm). However, niobium is not as compatible in a liquid sodium environment as the low alloy steel, but is protected from the sodium by the thin layer of nickel.

Regarding the construction of a nickel/niobium membrane, the essential concept to keep in mind are the thicknesses of the materials used and their composition. Both of these factors independently control the hydrogen diffusion rate. The exact method of their fabrication, i.e., mechanical fitting, electroplating, vapor deposition, sputtering, etc. is not important as the method of fabrication would not alter its function. For example, a thin layer of nickel has been successfully electroplated on a niobium tube and tests thereof have been successful in protecting the niobium from liquid sodium.

While particular embodiments and parameters have been illustrated and/or described, modifications will become apparent to those skilled in the art, and it is intended to cover in the appended claims all such modifications as come within the spirit and scope of the invention.

What we claim is:

1. In a hydrogen meter for measuring hydrogen concentration in liquid sodium comprising a diffusion tube assembly, ion pump means connected to create a vacuum within said diffusion tube assembly, and power supply and current readout means connected to said ion pump means; the improvement comprising said diffusion tube assembly being provided with a composite membrane consisting of a diffusion tube composed of 2¼ Cr-1 Mo steel, and a sleeve of essentially pure nickel about said diffusion tube.

2. The hydrogen meter defined in claim 1, wherein said diffusion tube has a wall thickness of about 10 mils, and wherein said sleeve has a wall thickness of about 4 mils.

3. The hydrogen meter defined in claim 1, wherein said diffusion tube assembly additionally includes a flange member and an end cap secured to each of said diffusion tube and said sleeve.

4. The hydrogen meter defined in claim 3, wherein said diffusion tube is secured in abutting relationship with said flange member and said end cap by weld joints, and wherein said sleeve is shrink fitted over said diffusion tube and securing in overlapping relationship with said flange member and said end cap by weld joints.

5. The hydrogen meter defined in claim 4, wherein said flange member and said end cap are constructed of stainless steel.

* * * * *